(12) United States Patent
Kim

(10) Patent No.: US 9,207,321 B2
(45) Date of Patent: Dec. 8, 2015

(54) ULTRASOUND SYSTEM HAVING VARIABLE LOOKUP TABLE AND METHOD FOR MANAGING VARIABLE LOOKUP TABLE

(75) Inventor: Sung Yoon Kim, Namyangju-si (KR)

(73) Assignee: SAMSUNG MEDISON CO., LTD., Hongcheon-Gun, Gangwon-Do (KR)

(*) Notice: Subject to any disclaimer, the term of this patent is extended or adjusted under 35 U.S.C. 154(b) by 688 days.

(21) Appl. No.: 12/727,982

(22) Filed: Mar. 19, 2010

(65) Prior Publication Data
US 2011/0040182 A1    Feb. 17, 2011

(30) Foreign Application Priority Data
Aug. 17, 2009  (KR) .................. 10-2009-0075853

(51) Int. Cl.
| A61B 8/00 | (2006.01) |
| G01S 15/89 | (2006.01) |
| A61B 8/08 | (2006.01) |
| G01S 7/52 | (2006.01) |
| G06T 15/08 | (2011.01) |

(52) U.S. Cl.
CPC ............. *G01S 15/8993* (2013.01); *A61B 8/466* (2013.01); *A61B 8/483* (2013.01); *G01S 7/52044* (2013.01); *G06T 15/08* (2013.01)

(58) Field of Classification Search
CPC ...... A61B 8/483; A61B 8/463; A61B 8/5238; A61B 8/00; A61B 6/463
USPC .......... 600/407, 437–472; 382/128, 130–134, 382/173, 174, 254–308, 318–321
See application file for complete search history.

(56) References Cited

U.S. PATENT DOCUMENTS

| 5,315,512 | A  | * | 5/1994 | Roth ........................... 600/442 |
| 6,193,661 | B1 |   | 2/2001 | Clark et al. |
| 6,530,885 | B1 | * | 3/2003 | Entrekin et al. ............. 600/437 |
| 2004/0138560 | A1 | * | 7/2004 | Paladini ...................... 600/437 |
| 2004/0147841 | A1 |   | 7/2004 | McLaughlin et al. |
| 2006/0100512 | A1 |   | 5/2006 | Lee |
| 2007/0167779 | A1 |   | 7/2007 | Kim et al. |

FOREIGN PATENT DOCUMENTS

| KR | 10-0856042 B1 | 9/2008 |
| KR | 10-0875414 B1 | 12/2008 |

OTHER PUBLICATIONS

Korean Office Action, w/ English translation thereof, issued in Korean Patent Application No. KR 10-2009-0075853 dated Aug. 12, 2011.

(Continued)

*Primary Examiner* — Mark Remaly
(74) *Attorney, Agent, or Firm* — McDermott Will & Emery LLP

(57) ABSTRACT

Disclosed is an ultrasound system including a variable lookup table. The ultrasound system includes the variable lookup table, a data acquiring unit to acquire ultrasound data, a lookup table generating unit to generate a variable lookup table according to the acquired ultrasound data, a three-dimensional (3D) rendering unit to perform 3D rendering with reference to the generated variable lookup table, and a display unit to display the 3D rendering result.

5 Claims, 3 Drawing Sheets

(56) References Cited

OTHER PUBLICATIONS

Search Report ssued on Nov. 29, 2012 in European Patent Application No. 10152638.2.

Johnny Kuo et al., "Interactive Volume Rendering of Real-Time Three-Dimensional Ultrasound Images", IEEE Transactions on Ultrasonics, Ferroelectrics, and Frequency Control, vol. 54, No. 2, Feb. 2007.

* cited by examiner

ULTRASOUND SYSTEM HAVING VARIABLE LOOKUP TABLE AND METHOD FOR MANAGING VARIABLE LOOKUP TABLE

CROSS-REFERENCE TO RELATED APPLICATION

This application claims the benefit of Korean Patent Application No. 10-2009-0075853, filed on Aug. 17, 2009, in the Korean Intellectual Property Office, the disclosure of which is incorporated herein by reference.

BACKGROUND

1. Field

The present invention relates to an ultrasound system having a variable lookup table and a variable lookup table managing method, and more particularly, to a variable lookup table managing method and an ultrasound system having a variable lookup table that stores each sampling location during a three-dimensional (3D) scan conversion, focuses on ultrasound data to be in different sizes based on the location, and gradually decreases a size of the ultrasound data of a location where a focus is on based on the size of the ultrasound data of the location where the focus is on when the focus progresses back and forth.

2. Description of the Related Art

Generally, an ultrasound system transmits an ultrasound signal to a predetermined internal part of a body from a surface of a target object, and acquires an image related to a section of a soft tissue or a blood vessel by using information of an ultrasound signal that is reflected from a tissue inside of the body.

The ultrasound system is small and inexpensive, and has a high stability since it has no coated wire, and thus, the ultrasound system is widely used together with an X-ray diagnostic device, a computerized tomography (CT) scanner, a magnetic resonance image (MRI) device, a nuclear medicine diagnostic device, and the like. In particular, the ultrasound system may display the internal part of the body in real-time, and thus, may have various types of usage.

As an area where the ultrasound system is utilized expands, various demands with respect to an ultrasound image provided by the ultrasound system continuously exist. In particular, the ultrasound system needs to obtain a three-dimensional (3D) ultrasound image, since a close observation of a lesion or a tissue of a patient is required to perform a medical examination, a biopsy, an operation, and the like.

The ultrasound system requires a 3D scan conversion to use a 3D volume rendering technology. However, the conventional ultrasound system computes a value through a trigonometrical function value, thereby having a problem of expending a great deal of time. Also, the conventional ultrasound system has a problem that a wood grain artifact, which is a sampling artifact, is generated during the 3D rendering operation. Also, to provide perspective, various attempts have been made for the 3D volume rendering in the ultrasound system.

SUMMARY

An aspect of the present invention provides an ultrasound system that has a three-dimensional (3D) lookup table that stores a location of each sampling during a 3D scan conversion and a variable lookup table managing method.

Another aspect of the present invention provides a variable lookup table managing method and an ultrasound system including a lookup table that sets, to 1, a size of ultrasound data of a location where a focus is on and gradually decreases the size of the ultrasound data of the location where the focus is on when the focus progresses back and forth.

According to example embodiments, there may be provided an ultrasound system, including a data acquiring unit to acquire ultrasound data, a lookup table generating unit to generate a variable lookup table according to a location of the acquired ultrasound data, a 3D rendering unit to perform 3D rendering with reference to the generated variable lookup table, and a display unit to display a result of the 3D rendering.

Also, the lookup table generating unit generates the variable lookup table that stores a location where a sampling is performed with respect to the acquired ultrasound data.

Also, the variable lookup table focuses on the acquired ultrasound data to have different sizes based on the location.

Also, the variable lookup table gradually decreases a size of the acquired ultrasound data based on the size of the acquired ultrasound data of a location where a focus is on, when the focus progresses back and forth.

Also, the ultrasound system further comprises a changing unit to change a location according to a request from a user, and the lookup table generating unit regenerates the variable lookup table based on the changed location.

According to example embodiments, there may be provided a method of managing a variable lookup table in an ultrasound system comprising a data acquiring unit, a lookup table generating unit, a 3D rendering unit, and a display unit, the method including acquiring, by the data acquiring unit, ultrasound data, generating, by the lookup table generating unit, the variable lookup table according to a location of the acquired ultrasound data, performing, by the 3D rendering unit, 3D rendering with reference to the generated variable lookup table, and displaying, by the display unit, a result of the 3D rendering.

Additional aspects and/or advantages will be set forth in part in the description which follows and, in part, will be apparent from the description, or may be learned by practice of the embodiments.

EFFECT

According to the present invention, there may be provided an ultrasound system that enables an image of a location where a focus is on to be clear, and a back and a forth of the image is out of focus, thereby having a fade-out effect.

Also, the present invention naturally acquires an interpolation effect during sampling, and thus, a wood grain artifact is eliminated, and a lookup table is minimally used.

BRIEF DESCRIPTION OF THE DRAWINGS

These and/or other aspects and advantages will become apparent and more readily appreciated from the following description of the embodiments, taken in conjunction with the accompanying drawings of which.

DETAILED DESCRIPTION

Figure 1:
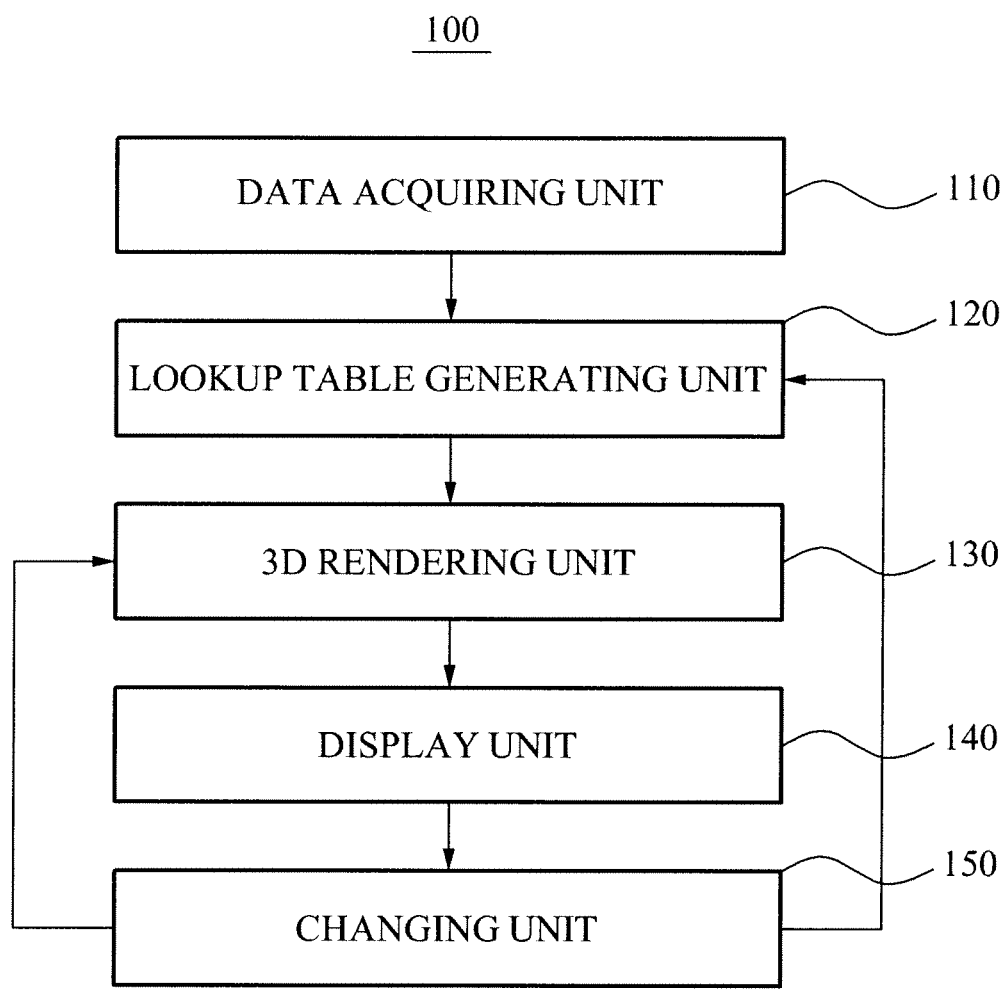
FIG. 1 is a diagram illustrating a configuration of an ultrasound system having a variable lookup table according to an exemplary embodiment of the present invention.

Reference will now be made in detail to example embodiments, examples of which are illustrated in the accompanying drawings, wherein like reference numerals refer to the like elements throughout. An ultrasound diagnosis apparatus utilizing a touch interaction is described below to explain the present disclosure by referring to the figures.

FIG. 1 is a diagram illustrating a configuration of an ultrasound system having a variable lookup table according to an exemplary embodiment of the present invention.

Referring to FIG. 1, the ultrasound system 100 according to an exemplary embodiment of the present invention includes a data acquiring unit 110, a lookup table generating unit 120, a 3D rendering unit 130, a display unit 140, and a changing unit 150.

The ultrasound system 100 may have a three-dimensional (3D) lookup table which stores a location of each sampling during a 3D scan conversion.

The data acquiring unit 110 may obtain ultrasound data with respect to a sample from the ultrasound system 100. That is, the data acquiring unit 110 acquires the ultrasound data with respect to the sample used for 3D scan conversion from the ultrasound system 100, and transfers the acquired ultrasound data to the lookup table generating unit 120.

Figure 2:
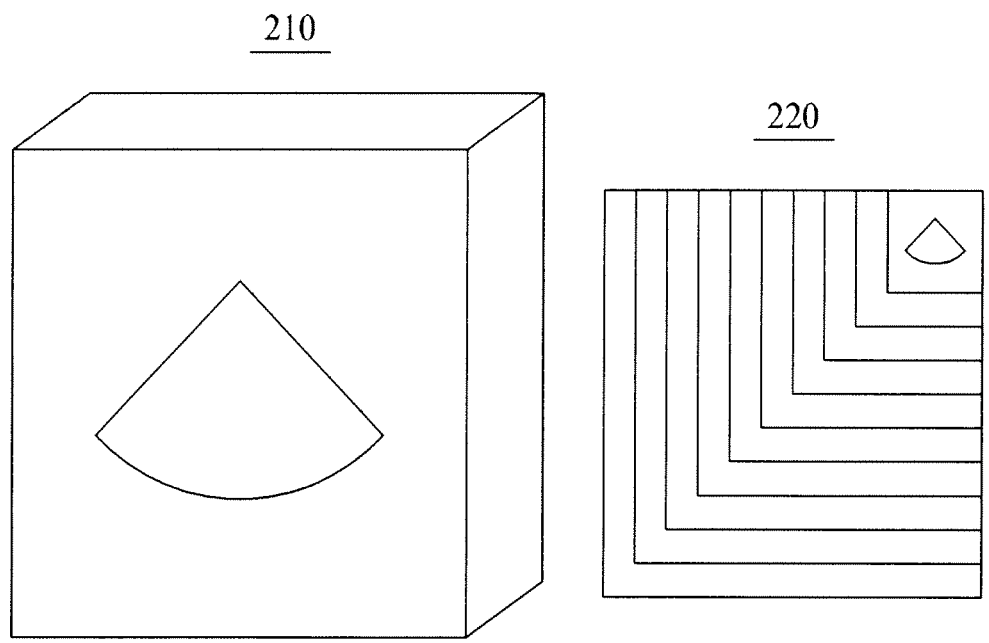
FIG. 2 is a diagram illustrating an example of a three-dimensional (3D) volume data and a variable lookup table according to an exemplary embodiment of the present invention.

FIG. 2 is a diagram illustrating an example of a 3D volume data and a variable lookup table according to an exemplary embodiment of the present invention.

Referring to FIG. 2, the 3D volume data 210 is 3D-scanned sample data in ultrasound system 100, and the variable lookup table 220 stores a location of each sampling during the 3D scan conversion.

The lookup table generating unit 120 generates a variable lookup table based on a location of the acquired ultrasound data. That is, the lookup table generating unit 120 receives the acquired ultrasound data from the data acquiring unit 110, and generates the variable lookup table where a location of sampling with respect to the ultrasound data is stored. The variable lookup table focuses on the acquired ultrasound data to have different sizes based on the location. Also, the variable lookup table gradually decreases a size of the acquired ultrasound data based on the size of the acquired ultrasound data of a location where a focus is on, when the focus progresses back and forth.

As an example, the variable lookup table sets, to 1, a size of the acquired ultrasound data of a location where the focus is on, the size being variable based on the location, and gradually decreases the size of the acquired ultrasound data of the location where the focuses is on, when the focus progressed back and forth. An image of the location where the focus is on is clear, and a back and a forth of the image is out of focus, thereby having a fade-out effect.

The 3D rendering unit 130 may perform a 3D rendering with reference to the generated lookup table. That is, the 3D rendering unit 130 receives the lookup table from the lookup table generating unit 120, and performs the 3D rendering with respect to the acquired ultrasound data with reference to the lookup table, and transfers a result of the 3D rendering to the display unit 140.

The display unit 140 displays the result of the 3D rendering. That is, the display unit 140 receives the result of the 3D rendering from the 3D rendering unit 130, and displays the result of the 3D rendering.

The changing unit 150 changes a location of the acquired ultrasound data based on a request from a user. That is, the changing unit 150 reports, to the lookup table generating unit 120 or the 3D rendering unit 130, whether the location is changed based on the request from the user.

The lookup table generating unit 120 regenerates the variable lookup table by changing the size based on the changed location. That is, the lookup table generating unit 120 determines whether the location is changed from the changing unit 150, and regenerates the variable lookup table based on a changed location, when the location is changed.

The 3D rendering unit 130 performs 3D rendering with reference to the regenerated variable lookup table. Also, when the location is not changed, the 3D rendering unit 130 performs rendering with reference to the existing variable lookup table.

As described in the above description, the ultrasound system 100 enables an image of a location where a focus is on to be clear, and enables a back and forth of the image to be out of focus, thereby having a fade out effect.

Also, the ultrasound system 100 naturally acquires an interpolation effect during the sampling, and thus, a wood grain artifact is eliminated and a lookup table is minimally used.

Figure 3:
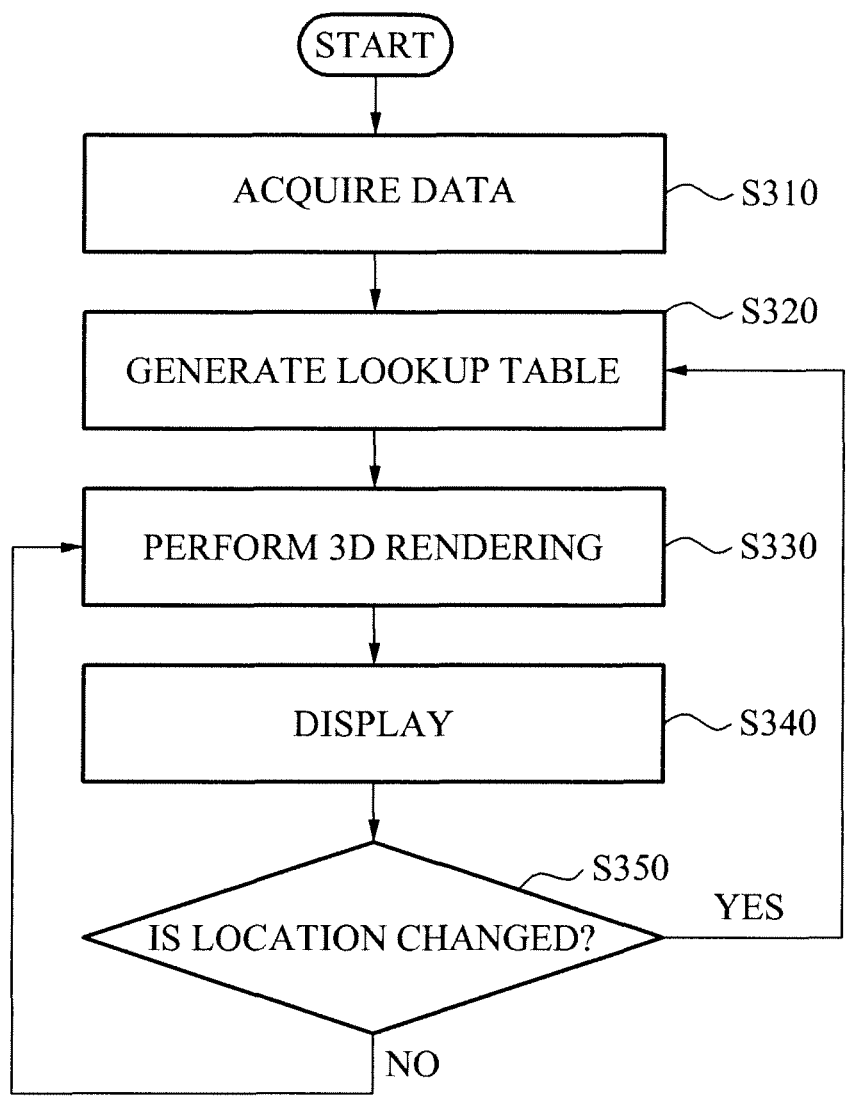
FIG. 3 is a flowchart illustrating a method of managing a variable lookup table according to an exemplary embodiment of the present invention.

FIG. 3 is a flowchart illustrating a method of managing a variable lookup table according to an exemplary embodiment of the present invention.

Referring to FIGS. 1 through 3, the ultrasound system 100 acquires ultrasound data in operation S310. That is, the ultrasound system 100 acquires the ultrasound data via the data acquiring unit 110 in operation S310.

In operation S320, the ultrasound system 100 generates a variable lookup table based on a location of the acquired ultrasound data. That is, in operation S320, the ultrasound system 100 generates, through the lookup table generating unit 120, the variable lookup table that enables the acquired ultrasound data to have different size based on the location of the acquired ultrasound data. As an example, in operation S320, the ultrasound system 100 may generate, through the lookup table generating unit 120, the variable lookup table where a location of sampling with respect to the ultrasound data is stored. The variable lookup table may focus on the ultrasound data to be in different sizes based on the location. Also, the variable lookup table may gradually decreases a size of the ultrasound data based on the size of the ultrasound data of a location where a focus is on, when the focus progresses back and forth.

As an example, in operation S320, the ultrasound system 100 enables, through the lookup table generating unit, the lookup table to set, to 1, the size of the acquired ultrasound data of the location where the focus is on, the size being variable based on the location, and gradually decreases the size of the acquired ultrasound data of the location where the focuses is on, when the focus progressed back and forth. An image of the location where the focus is on is clear, and a back and a forth of the image is out of focus, thereby having a fade out effect.

In operation S330, the ultrasound system 100 performs 3D rendering with reference to the variable lookup table. That is, in operation S330, the ultrasound system 100 performs, through the 3D rendering unit 130, the 3D rendering with respect to the acquired ultrasound data with reference to the generated lookup table.

In operation S340, the ultrasound system 100 displays a result of the 3D rendering. That is, in operation S340, the ultrasound system 100 displays, through the display unit 140, the result of the 3D rendering.

In operation S350, the ultrasound system 100 determines whether to change a location based on a request from a user. That is, in operation S350, the ultrasound system 100 determines, through the changing unit 150, whether to change the location based on the request from the user.

When the location is determined to be changed, the ultrasound system 100 proceeds again with operation S320 to regenerate the variable lookup table based on the changed location. Also, the ultrasound system 100 performs the 3D rendering based on the variable lookup table regenerated based on the changed location.

Conversely, when the location is determined to not be changed, the ultrasound system 100 proceeds again with operation S330 and performs the 3D rendering with reference to the existing variable lookup table.

As described in the above description, a variable lookup table managing method in the ultrasound system enables an image of a location where a focus is on to be clear, and a back and a forth of the image is out of focus, thereby having a fade-out effect.

Also, the variable lookup table managing method in the ultrasound system naturally acquires an interpolation effect during sampling, and thus, a wood grain artifact is eliminated and a lookup table is minimally used.

The variable lookup table managing method according to the above-described example embodiments may be recorded in computer-readable media including program instructions to implement various operations embodied by a computer. The media may also include, alone or in combination with the program instructions, data files, data structures, and the like. Examples of computer-readable media include magnetic media such as hard disks, floppy disks, and magnetic tape; optical media such as CD ROM disks and DVDs; magneto-optical media such as optical disks; and hardware devices that are specially configured to store and perform program instructions, such as read-only memory (ROM), random access memory (RAM), flash memory, and the like. Examples of program instructions include both machine code, such as produced by a compiler, and files containing higher level code that may be executed by the computer using an interpreter. The described hardware devices may be configured to act as one or more software modules in order to perform the operations of the above-described example embodiments, or vice versa.

Although a few example embodiments have been shown and described, it would be appreciated by those skilled in the art that changes may be made in these example embodiments without departing from the principles and spirit of the invention, the scope of which is defined in the claims and their equivalents.

What is claimed is:

1. An ultrasound system, comprising:
a hardware processor;
a display coupled to the hardware processor; and
computer-readable memory comprising programs that, when executed by the hardware processor, perform operations comprising:
acquiring ultrasound data on Cartesian coordinates with respect to a sample, on spherical coordinates, such that the spherical coordinates undergo a three-dimensional (3D) conversion to the Cartesian coordinates;
generating a variable lookup table according to a location of the sample on the spherical coordinates corresponding to the acquired ultrasound data;
performing 3D rendering with reference to the generated variable lookup table; and
displaying a result of the 3D rendering,
wherein the variable lookup table stores the location of the sample and,
wherein the generating the variable lookup table comprises:
generating variable lookup tables in various sizes based on the spherical coordinates of the sample,
wherein the variable lookup table:
sets a size of a first lookup table to 1 generated corresponding to a location where the focus is on, and
gradually decreases a size of at least another lookup table, wherein the another lookup table is generated corresponding to a location close to the location corresponding to the first lookup table.

2. The ultrasound system of claim 1, wherein the programs that perform the operation comprise:
selecting a different sample location on the acquired ultrasound data according to a request from a user;
regenerating the variable lookup table according to the selected sample location;
performing another 3D rendering with reference to the regenerated variable lookup table; and
displaying another result of the another 3D rendering.

3. A method of managing a variable lookup table in an ultrasound system comprising a hardware processor which executes the method, the method comprising:
acquiring ultrasound data on Cartesian coordinates with respect to a sample on Cartesian coordinates used for 3D scan conversion from the spherical coordinates to the Cartesian coordinates;
generating the variable lookup table according to a location of the sample on the spherical coordinates corresponding to the acquired ultrasound data;
performing 3D rendering, with reference to the generated variable lookup table; and
displaying a result of the 3D rendering,
wherein the variable lookup table stores the location of the sample;
generating variable lookup tables in various sizes based on the spherical coordinates of the sample,
wherein the variable lookup table sets a size of a first lookup table to 1 generated corresponding to a location where the focus is on, and
gradually decrease a size of at least another lookup table, wherein the another lookup table is generated corresponding to a location close to the location corresponding to the first lookup table.

4. The method of claim 3, wherein:
the method further comprises:
selecting a different sample location on the acquired ultrasound data according to a request from the user;
regenerating the variable lookup table according to the selected sample location;
performing another 3D rendering, with reference to the regenerated variable lookup table; and
displaying another result of the another 3D rendering.

5. A non-transitory computer readable recoding medium storing a program implementing the method of claim 3.

* * * * *